(12) United States Patent
Iida et al.

(10) Patent No.: US 11,606,985 B2
(45) Date of Patent: Mar. 21, 2023

(54) SUPPORTER

(71) Applicant: KOWA COMPANY, LTD., Nagoya (JP)

(72) Inventors: Takuji Iida, Gose (JP); Itsuo Nagata, Gose (JP); Yukihiro Hosoe, Tokyo (JP)

(73) Assignee: KOWA COMPANY, LTD., Nagoya (JP)

( * ) Notice: Subject to any disclaimer, the term of this patent is extended or adjusted under 35 U.S.C. 154(b) by 0 days.

(21) Appl. No.: 17/275,568

(22) PCT Filed: Sep. 13, 2019

(86) PCT No.: PCT/JP2019/036028
§ 371 (c)(1),
(2) Date: Mar. 11, 2021

(87) PCT Pub. No.: WO2020/054832
PCT Pub. Date: Mar. 19, 2020

(65) Prior Publication Data
US 2022/0095714 A1 Mar. 31, 2022

(30) Foreign Application Priority Data

Sep. 13, 2018 (JP) .............................. JP2018-171890

(51) Int. Cl.
*A61F 13/10* (2006.01)
*A41D 13/08* (2006.01)

(52) U.S. Cl.
CPC .......... *A41D 13/087* (2013.01); *A61F 13/104* (2013.01)

(58) Field of Classification Search
CPC .... A41D 13/087; A41D 13/08; A41D 13/002; A41D 13/0015; A61F 13/104
See application file for complete search history.

(56) References Cited

U.S. PATENT DOCUMENTS 2,949,610 A * 8/1960 Lutsky ................. A63B 71/148
473/59
6,155,084 A 12/2000 Andrews et al.
(Continued)

FOREIGN PATENT DOCUMENTS

EP 3287103 A1 2/2018
JP 63-027418 U 2/1988
(Continued)

OTHER PUBLICATIONS

English Language Translation of JP4-343868A (Year: 1997) provided by Espacenet Mar. 4, 2021; Wacoal Corp; Fujimoto Masami.*
(Continued)

*Primary Examiner* — Clinton T Ostrup
*Assistant Examiner* — Akwokwo Olabisi Redhead
(74) *Attorney, Agent, or Firm* — Knobbe, Martens, Olson & Bear LLP

(57) ABSTRACT

The finger supporter is disclosed. The finger supporter includes: a first anchor portion 2 that is formed at an upper end 10a of a tubular fabric and causes the tubular fabric to be fastened to a forearm wrist portion of a wearer; a second anchor portion 3 that is formed to continue two points of a circling portion on the other end side of the tubular fabric and forms the circling portion into two opening portions 12a and 12b with different sizes; and a first support portion 4 that couples the second anchor portion 3 and the first anchor portion 2 and supports any one finger inserted into the smaller opening portion 12a from among five fingers.

10 Claims, 5 Drawing Sheets

(56) References Cited

U.S. PATENT DOCUMENTS

| | | | | |
|---|---|---|---|---|
| 7,895,671 | B2* | 3/2011 | Salomon | A41D 13/087 2/163 |
| 2004/0060096 | A1* | 4/2004 | Thiruppathi | A41D 13/088 2/160 |
| 2008/0271224 | A1* | 11/2008 | Wilbert | A41D 19/01523 2/163 |
| 2010/0022930 | A1* | 1/2010 | Koby | A61F 5/0118 602/21 |
| 2012/0283610 | A1* | 11/2012 | Matsuo | A61F 13/104 602/21 |

FOREIGN PATENT DOCUMENTS

| | | |
|---|---|---|
| JP | 01-129209 U | 9/1989 |
| JP | 4-343868 A | 11/1992 |
| JP | 6-285108 A | 10/1994 |
| JP | 2013-104139 A | 5/2013 |
| JP | 2013104139 | 5/2013 |
| TW | M356398 U | 5/2009 |
| TW | M485716 U | 9/2014 |
| WO | WO 2018/154062 A1 | 8/2018 |

OTHER PUBLICATIONS

English Language Translation of JP2013-104139A (Year: 2013) provided by Espacenet Mar. 11, 2021; Molten Corp; Motohiro et al.*

English Language Translation of JP1208971986 (Year: 1986) provided by J-Plat-Pat Mar. 5, 2021; Takasaki Yashima Toshio.*

Extended European Search Report in Application No. 19860823.4, dated Mar. 16, 2022.

Office Action received in TW Application No. 108132999, dated Jan. 4, 2023.

* cited by examiner

SUPPORTER

TECHNICAL FIELD

The present invention relates to a supporter that reduces a load on any one finger from among five fingers of a wearer.

BACKGROUND ART

As supporters for hand joints, techniques described in Patent Literatures 1 and 2, for example, have been disclosed. According to the technique described in Patent Literature 1, a hand joint supporter 10 includes: a first anchor portion 2 that causes a corresponding tubular knitted fabric to be fastened to a forearm of a wearer; a second anchor portion 3 that allows a thumb 21 of a hand of the wearer to be inserted and circles around a portion corresponding to a proximal phalanx 21b of the thumb 21; a first support portion 4 that is formed between the first anchor portion 2 and the second anchor portion 3, passes through a portion corresponding to a pisiform bone 26 of the wearer from the second anchor portion 3 on the palm side of the wearer via the back-of-hand side of the wearer, extends up to the first anchor portion 2 on the palm side of the wearer via the palm side of the wearer, and is made of a spiral knitted fabric; and a base fabric portion 1 that is a knitted fabric except for the first anchor portion 2, the second anchor portion 3, and the first support portion 4 of the tubular knitted fabric, the knitted fabric having a stretch resistance that is weaker than a stretch resistance of the first support portion 4.

According to the technique described in Patent Literature 2, a hand joint supporter 10 includes: a first anchor portion 2 that causes a tubular knitted fabric to be fastened to a forearm; a second anchor portion 3 that causes the tubular knitted fabric to be fastened to a palm and a back of the hand; a hole anchor portion 11 that is formed as a throughhole with a substantially circular shape in the vicinity of the second anchor portion 3 in the tubular knitted fabric and allows a thumb of the hand to be inserted; and a support portion 4 that is formed to extend in a length direction of the tubular knitted fabric with a portion corresponding to a carpometacarpal joint straddled, on a front side and/or a back side of the tubular knitted fabric, is coupled to the first anchor portion 2 and the hole anchor portion 11, and supports hand joints, a stretch resistance of the first anchor portion 2 in a circumferential direction of the tubular knitted fabric being stronger than a stretch resistance of a base fabric portion 1 in the circumferential direction of the tubular knitted fabric, a stretch resistance of the support portion 4 in the length direction of the tubular knitted fabric being stronger than a stretch resistance of the base fabric portion 1 in the length direction of the tubular knitted fabric.

CITATION LIST

Patent Literature

Patent Literature 1: Japanese Patent Laid-Open No. 2013-104139
Patent Literature 2: Japanese Patent No. 5543496

SUMMARY OF INVENTION

Technical Problem

However, according to the technique described in Patent Literature 1, the second anchor portion into which the thumb of the wearer is to be inserted is sewn by a sewing machine with a cut made in the tubular knitted fabric and with a cut edge folded back to the inside of the tubular knitted fabric, and the sewn portion thus stimulates the surface of the thumb of the wearer and leads to a poor feeling of wearing.

Also, although there is a description that the tubular knitted fabric may be formed through knitting without sewing the sewn portion, it is significantly difficult to separately form the second anchor portion through knitting, and even if it is possible to form the second anchor portion through knitting, the manufacturing is significantly complicated, which leads to deterioration of manufacturing efficiency.

Although the technique described in Patent Literature 2 can improve stability of hand joints and reduce a load on the hand joints, it is not possible to reduce a load on muscles or joints that support a wrist or any one finger by curbing motions such as adduction and abduction of the wrist and bending and stretching movements of fingers at interphalangeal joints.

The present invention provides a supporter capable of stabilizing hand joints of a wearer and reducing a load on muscles or joints that support any one finger.

Solution to Problem

A supporter according to the present invention includes: a first anchor portion that is formed on one end side of a tubular fabric and causes the tubular fabric to be fastened to a forearm wrist portion of a wearer; a second anchor portion that is formed to couple two points of a circling portion on the other end side of the tubular fabric and forms the circling portion into at least two opening portions with different sizes; and a first support portion that is supported between the second anchor portion and the first anchor portion and supports any one finger inserted into a smaller one of the opening portions from among five fingers.

Since the supporter according to the present invention includes: the first anchor portion that is formed on the one end side of the tubular fabric and causes the tubular fabric to be fastened to the forearm wrist portion of the wearer; a second anchor portion that is formed to couple the two points of the circling portion on the other end side of the tubular fabric and forms the circling portion into two opening portions with different sizes; and the first support portion that is supported between the second anchor portion and the first anchor portion and supports any one finger inserted into a smaller one of the openings from among five fingers as described above, an effect that makes it possible to reduce a load on a wrist and fingers of the wearer with the first support portion is achieved. In particular, an effect that makes it possible to reduce a load on muscles or joints that support any one finger and to curb inflammations such as an inflammation of the tendon sheath is achieved by curbing bending and stretching movements of any one finger at an interphalangeal joint.

In the supporter according to the present invention, the second anchor portion is preferably formed to couple the two points of the circling portion on the other end side of the tubular fabric.

Since the second anchor portion is formed to couple the two points of the circling portion on the other end side of the tubular fabric in the supporter according to the present invention as described above, an effect that makes it possible to form the opening portions with different sizes only through a simple operation while realizing functions of the anchor portion is achieved.

In the supporter according to the present invention, the second anchor portion is preferably formed to be located between a metacarpophalangeal joint and a proximal interphalangeal joint or an interphalangeal joint of the any finger of the wearer.

Since the second anchor portion is formed to be located between the metacarpophalangeal joint and the proximal interphalangeal joint or the interphalangeal joint of the any finger of the wearer, in the supporter according to the present invention as described above, a tensile force of supporting the any finger from the palm side to the back-of-hand side is applied to the position between the metacarpophalangeal joint and the proximal interphalangeal joint or the interphalangeal joint of the any finger with the first support portion, and an effect that makes it possible to reduce a load on muscles or joints of the any finger on the palm side is achieved.

In the supporter according to the present invention, the first support portion preferably passes through one side surface and/or the other side surface of the any finger of the wearer from a vicinity of the second anchor portion and is then supported by the first anchor portion.

Since the first support portion passes through the one side surface and/or the other side surface of the any finger of the wearer from the vicinity of the second anchor portion and is then supported by the first anchor portion in the supporter according to the present invention as described above, an effect that makes it possible to stabilize the any finger of the wearer and to apply a sufficient tensile force to the any finger on the back-of-hand side is achieved.

In the supporter according to the present invention, a corresponding region from the second anchor portion to a metacarpophalangeal joint of the any finger on a back-of-hand side of the wearer is formed with a fabric that has a weaker stretch resistance at least in a length direction of the tubular fabric than the first support portion.

Since the corresponding region from the second anchor portion to the metacarpophalangeal joint of the any finger on the back-of-hand side of the wearer is formed with the fabric that has a weaker stretch resistance at least in the length direction of the tubular fabric than the first support portion in the supporter according to the present invention as described above, the supporter is not unnecessarily strongly fastened to the any finger of the wearer, and an effect that makes it possible to improve a feeling of wearing is thus achieved.

In the supporter according to the present invention, the any finger is preferably a thumb, and the supporter preferably includes a second support portion that supports a region corresponding to outside of a little finger of the wearer.

Since the any finger is the thumb, and the supporter includes the second support portion that supports the region corresponding to the outside of the little finger of the wearer in the supporter according to the present invention as described above, an effect that the little finger side is also stably supported in addition to the stabilization of the thumb and it is thus possible to reduce a load on the entire hand is achieved. In other words, it is possible to support the wrist from both sides with the first support portion and the second support portion, to curb motions such as adduction and abduction of the wrist, and thereby to curb inflammations such as an inflammation of the tendon sheath of the wrist.

In the supporter according to the present invention, a larger opening portion of the two opening portions with different sizes formed by the second anchor portion is formed linearly or with a curve on a wrist side in an oblique direction from the second anchor portion toward the wrist side at a position of a peripheral edge of the larger opening portion which faces the second anchor portion.

Since the larger opening portion of the two opening portions with different sizes formed by the second anchor portion is formed linearly or with a curve on the wrist side in the oblique direction from the second anchor portion toward the wrist side at the position of the peripheral edge of the larger opening portion which faces the second anchor portion in the supporter according to the present invention as described above, an effect that makes it possible to smoothly perform operations with fingers on a keyboard, for example, is achieved. In particular, an effect that makes it possible to bring the edge portion of the opening into close contact with the surface of the thenar eminence such that the edge portion follows the surface of the thenar eminence by forming the opening portion with a curve on the wrist side, thereby improving a feeling of wearing of the wearer and enabling stable wearing is achieved.

In the supporter according to the present invention, wherein a smaller opening portion of the two opening portions with different sizes formed by the second anchor portion is preferably extended on an outer direction of the tubular fabric at least beyond a side surface of the first anchor portion of the tubular fabric.

Since the smaller opening portion of the two opening portions with different sizes formed by the second anchor portion is formed in the region extended in the outer direction of the tubular fabric at least beyond the side surface of the first anchor portion of the tubular fabric in the supporter according to the present invention as described above, in a case in which the thumb of the wearer is inserted into the smaller opening, the thumb of the wearer typically warps on the back-of-hand side when the thumb is stretched, and the extended portion is formed to be able to abut on the warp of the thumb and can thus improve a feeling of wearing of the wearer.

Also, in a case in which, for example, any of index to little fingers of the wearer is inserted into the smaller opening portion, a tensile force on the back-of-hand side increases for the one finger inserted into the smaller opening portion, and an effect that enables the one finger to be supported on the back-of-hand side is achieved.

In the supporter according to the present invention, the second anchor portion is preferably formed by being sewn from outside with at least two points on an inner side of the circling portion on the other end side of the tubular fabric adhering to each other.

Since the second anchor portion is formed by being sewn from the outside with the two points on the inner side of the circling portion on the other end side of the tubular fabric adhering to each other in the supporter according to the present invention as described above, an effect that makes it possible to prevent the stitched seam formed when the two points of the circling portion are sewn from coming into contact with the fingers of the wearer and degrading a feeling of wearing is achieved.

DESCRIPTION OF EMBODIMENTS

First Embodiment of Present Invention

Hereinafter, the present invention will be described in detail by exemplifying embodiments of the present invention. However, the present invention is not limited to the embodiments.

Figures 1A, 1B, 1C, 1D, 1E:
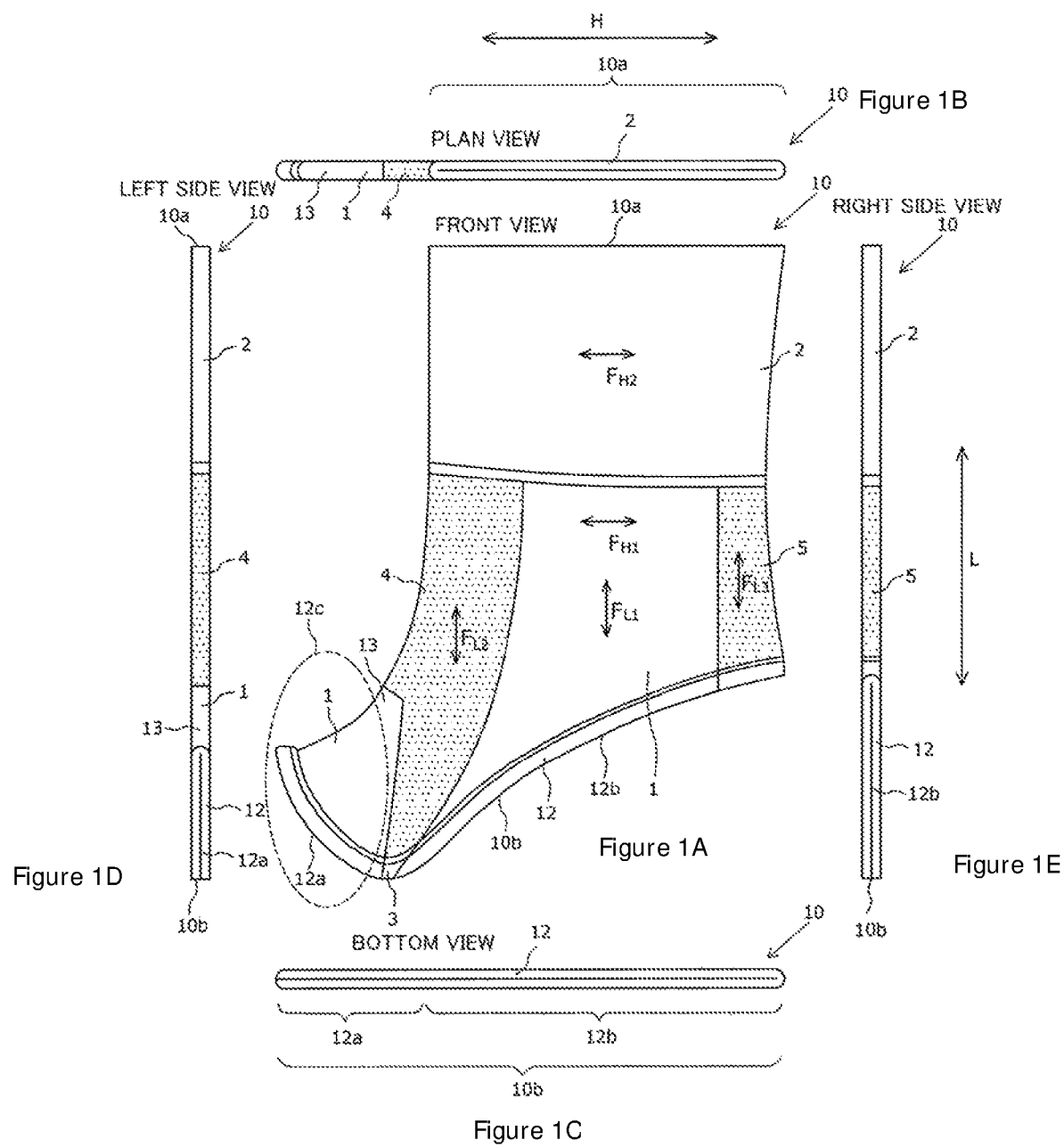
FIGS. 1A-1E illustrate five views of a supporter according to a first embodiment.
Figure 2:
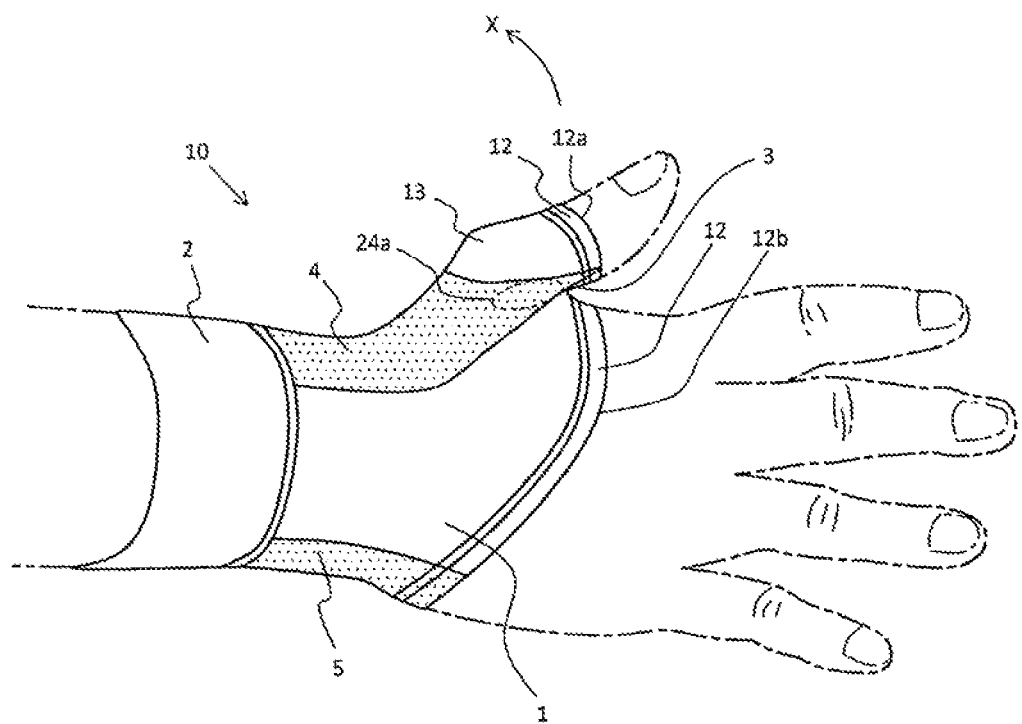
FIG. 2 is a first view illustrating a wearing state of the supporter according to the first embodiment.
Figure 3:
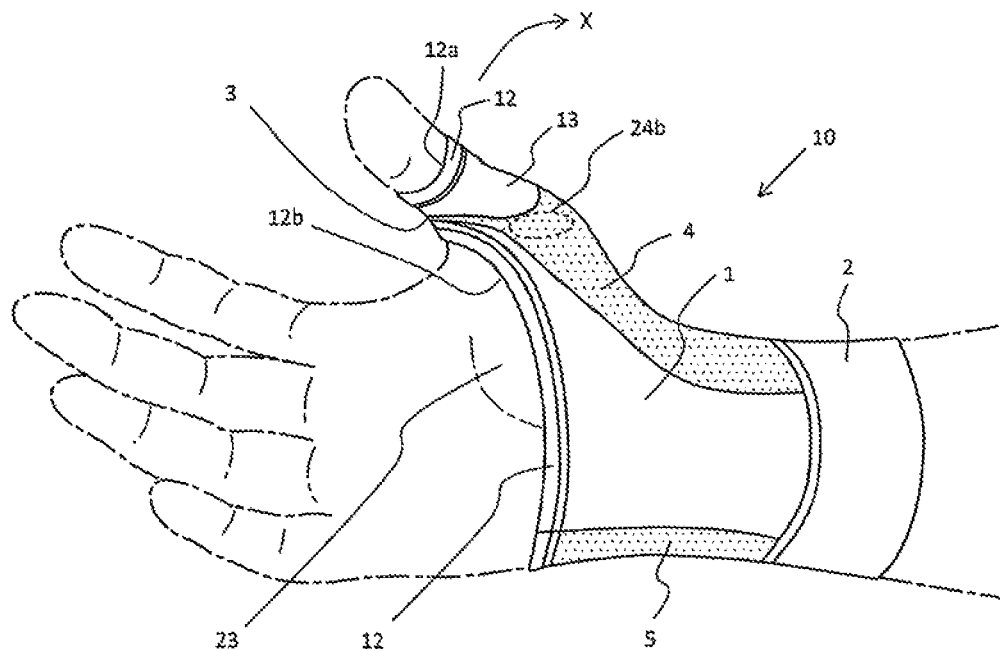
FIG. 3 is a second view illustrating a wearing state of the supporter according to the first embodiment.
Figure 4:
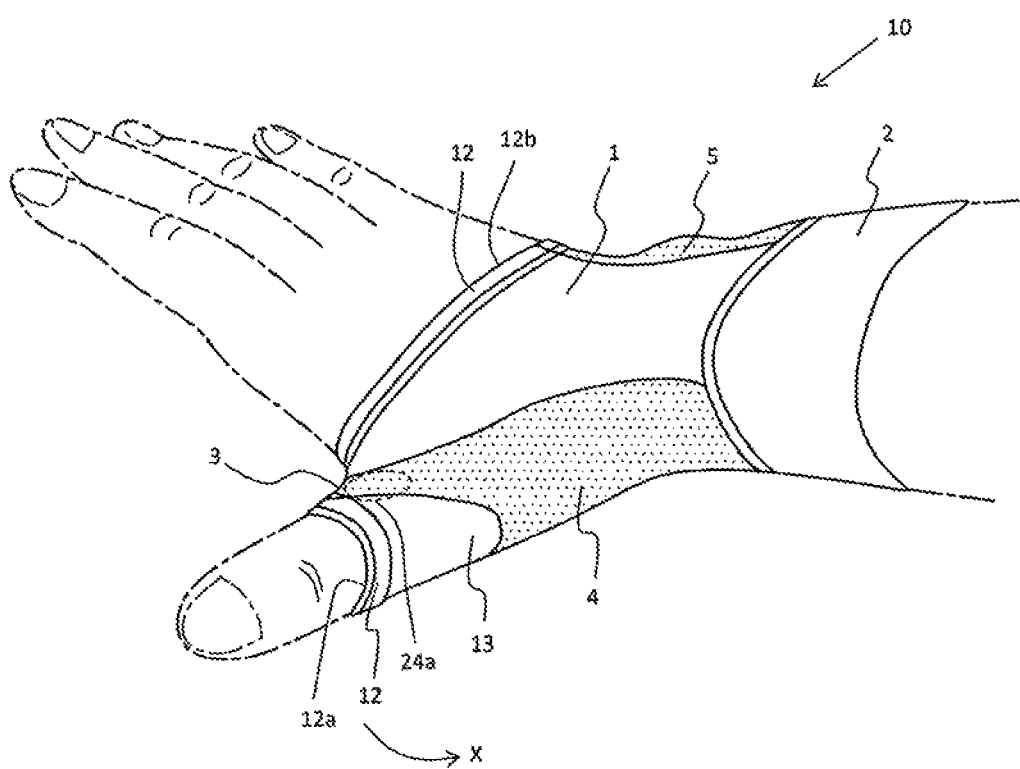
FIG. 4 is a third view illustrating a wearing state of the supporter according to the first embodiment.

A supporter according to the embodiment will be described with reference to FIGS. 1A to 4. FIGS. 1A-1E illustrate five views of the supporter according to the embodiment, and FIGS. 2 to 4 are diagrams illustrating wearing states of the supporter according to the embodiment. Note that although the back view is omitted in FIG. 1, the back view is obtained by horizontally flipping the front view.

The supporter according to the embodiment is a supporter mainly for fingers and is adapted to reduce a load on any one finger (thumb, for example) from among five fingers. In FIGS. 1 to 4, a finger supporter 10 is a supporter that is made, for example, of a tubular knitted fabric circularly knitted by a sock knitting machine (a knitting model manufactured by Lonati, for example), comes into close contact with a body surface of a wearer, supports movements of the hands or the thumb of the wearer, and reduces a load on the hand or the fingers of the wearer.

The finger supporter 10 is provided with desired functionality such as a taping function by applying a different type of knitting to a base fabric portion 1 that is a knitted fabric formed through plain knitting, rib-knitting, tuck knitting, float knitting, pile knitting, or the like using an upper thread, an under thread, and a rubber thread as knitting threads. Note that the base fabric portion 1 according to the embodiment is a knitted fabric formed through tuck knitting (hereinafter, referred to as a tuck-knitted fabric).

Note that although a case in which the finger supporter 10 is formed with a circularly knitted tubular knitted fabric will be described in the embodiment, the finger supporter 10 may be formed through warp knitting or sewing rather than the circular knitting, the tubular knitted fabric may be a woven fabric rather than the knitted fabric, a yarn used for the tubular knitted fabric may be formed of chemical fiber and the like in addition to natural fiber.

The finger supporter 10 is formed to circle around one end (upper end 10a) of the tubular knitted fabric and includes a first anchor portion 2 that causes the finger supporter 10 to be fastened to a forearm wrist portion of the wearer. The first anchor portion 2 is formed to have a stretch resistance in a circumferential direction H of the finger supporter 10 (tubular knitted fabric) that is stronger than a stretch resistance in the circumferential direction H of the base fabric portion 1 of the finger supporter 10. In other words, when a tensile force in a case in which constant stretching is applied in a state in which no stretching is applied to the material is defined as F, a tensile force in the circumferential direction H at the base fabric portion 1 of the finger supporter 10 is defined as $F_{H1}$, and a tensile force in the circumferential direction H at the first anchor portion 2 of the finger supporter 10 is defined as $F_{H2}$, a magnitude relationship of $F_{H2} > F_{H1}$ that means that the first anchor portion 2 has a higher fastening force in the circumferential direction H of the finger supporter 10 as compared with the base fabric portion 1 is preferably established.

Specifically, the first anchor portion 2 can have a stronger stretch resistance in the circumferential direction H of the finger supporter 10 relative to the base fabric portion 1 that is a tuck-knitted fabric by having a tacking-plain-knitted double structures or by being formed as a knitted fabric formed through moss knitting (hereinafter, referred to as a moss-knitted fabric).

Note that the moss-knitted fabric is a knitted fabric in which plain knitting and tuck knitting (arrangement in which knitted stitches are not allowed to escape along a certain course and a plurality of loops are allowed to escape in the following courses) appear alternately or every several courses in the course direction and the wale direction. Therefore, it is possible to create bumps or lace stitching in the first anchor portion 2 by employing the plain knitting and the tuck knitting in combination, and a moss-like knitted pattern appears.

In this manner, since the first anchor portion 2 is formed to circle around the forearm wrist portion of the wearer and has a stretch resistance in the circumferential direction H of the finger supporter 10 that is stronger than the stretch resistance of the base fabric portion 1 in the circumferential direction H of the finger supporter 10, it is possible to secure the finger supporter 10 to the forearm wrist portion of the wearer and to curb sliding-down and sliding-up of the upper end 10a of the finger supporter 10 at the time of palmar flexion of hand joints or due to bending and stretching movements of fingers. Moreover, the first anchor portion 2 supports a first support portion 4, which will be described later, and also functions as an anchor of the first support portion 4.

The finger supporter 10 includes a facing portion 12 formed into an S shape in a front view by folding back an opening portion at the other end (lower end 10b) of the tubular knitted fabric to the inside of the tubular knitted fabric and sewing the opening portion using a sewing machine. A second anchor portion 3 that forms the opening portion at the lower end 10b into two opening portions (opening portions 12a and 12b) with different sizes through sewing at two points of the circling portion of the formed facing portion 12 is included. At this time, it is possible to prevent the stitched seam formed due to the sewing from coming into direct contact with the fingers of the wearer and degrading a feeling of wearing, through sewing from the outside of the facing portion 12 with the two points on the inner side of the facing portion 12 adhering to each other to form the second anchor portion 3.

The second anchor portion 3 is formed to be attached to a portion between the metacarpophalangeal joint and the interphalangeal joint of the thumb of the wearer as illustrated in FIGS. 2 to 4, and a force is likely to act in the direction in which the thumb is extended (in the direction of adduction of the wrist (extending direction X)) due to the tensile force of the first support portion 4, which will be described later. If the second anchor portion 3 is located to be closer to the finger tip beyond the interphalangeal joint of the thumb at this time, for example, the tensile force for causing abduction of the wrist does not effectively act. Also, if the second anchor portion 3 is located at the metacarpophalangeal joint of the thumb, the tensile force of the first support portion 4 acts in a direction in which the thumb is closed, which leads to an adverse effect. Thus, the second anchor portion 3 is preferably regarded as being appropriately located when the second anchor portion 3 is between the metacarpophalangeal joint and the interphalangeal joint of the thumb of the wearer.

The opening portion 12a is for an opening portion for allowing the thumb of the wearer to be inserted therethrough, and the opening portion 12b is an opening portion for allowing index to little fingers index finger little finger of the wearer to be inserted therethrough. In other words, the sewing position of the second anchor portion 3 is determined such that the opening portion 12a through which the thumb is to be inserted is smaller than the opening portion 12b through which the index to little fingers are to be inserted.

The opening portion 12a has an extended portion 12c extended on the outer direction of the tubular knitted fabric beyond the side surface of the first anchor portion 2. Note that the extended portion 12c may be formed in the process of forming the tubular knitted fabric or may be formed using stretchiness of the knitted fabric. Moreover, the extended portion 12c may be formed by cutting a fabric. The thumb of the wearer typically warps on the back-of-hand side when stretched, and the extended portion 12c is formed to be able to abut on the warp of the thumb and can thus improve a feeling of wearing of the wearer.

Also, the opening portion 12b into which the index to little fingers are to be inserted is formed linear or with a curve on the wrist side in an oblique direction from the second anchor portion 3 toward the wrist side of the side surface on the little finger side of the wearer. In a case in which the opening portion 12b is not sewn in the oblique direction from the second anchor portion 3 toward the wrist side of the side surface on the little finger side of the wearer in this manner, there is a probability that the lower end 10b of the finger supporter 10 may restrict motions of the index to little fingers of the wearer, and this may cause problems in operations performed on a keyboard of a PC or the like. However, it is possible to allow the index to little fingers to freely move and smoothly perform operations by sewing the opening portion 12b in the oblique direction from the second anchor portion 3 toward the wrist side of the side surface on the little finger side of the wearer.

Further, in a case in which the opening portion 12b is formed with a curve on the wrist side in the oblique direction from the second anchor portion 3 toward the wrist side of the side surface on the little finger side of the wearer, the edge portion of the opening portion 12b follows the surface of the thenar eminence 23 of the wearer and can thus enhance a feeling of wearing, and even in a case in which the thumb is bent on the palm side, no space is generated between the thenar eminence 23 and the knitted fabric, and it is possible to wear the finger supporter with close contact. The facing portion 12 is formed into an S shape in front view, and it is possible to achieve an improvement in feeling of wearing as described above by forming the extended portion 12c at the opening portion 12a and forming the opening portion 12b linearly or with a curve on the wrist side in the oblique direction from the second anchor portion 3 toward the wrist side of the side surface on the little finger side of the wearer as described above.

The first support portion 4 passes through a region from one side surface of the thumb of the wearer to the root portion (the region of the side surface on the back-of-hand side and the root portion of the thumb, and this will be referred to as a first region below) 24a and/or a region from the other side surface to the root portion (the region of the side surface on the palm side and the root portion of the thumb, and this will be referred to as a second region below) 24b from the vicinity of the second anchor portion 3, is then supported by the first anchor portion 2, and supports the thumb of the wearer in a direction in which the thumb is extended (the direction of abduction of the wrist (the extending direction X)). In other words, the first support portion 4 is supported in the vicinity of the first anchor portion at the forearm wrist portion of the wearer on one end side and is supported in the vicinity of the second anchor portion 3 on the other end side. Note that the first support portion 4 may be formed with the one end side coupled directly to the first anchor portion 2 or may be formed with a separation of one or a plurality of courses (within a range in which the support force of the first anchor portion 2 reaches the first support portion 4). Similarly, the first support portion 4 may be formed with the other end side coupled directly to the second anchor portion 3 or may be formed to be supported in the vicinity of the second anchor portion 3 (within a range in which the support force of the second anchor portion 3 reaches the first support portion 4).

The first support portion 4 is formed such that a stretch resistance thereof in a length direction L of the finger supporter 10 is stronger than a stretch resistance of the base fabric portion 1 in the length direction L of the finger supporter 10. In other words, in a case in which the tensile force of the base fabric portion 1 in the length direction L of the finger supporter 10 is defined as $F_{L1}$, and the tensile force of the first support portion 4 in the length direction L of the finger supporter 10 is defined as $F_{L2}$, a magnitude relationship of $F_{L2} > F_{L1}$ that means that the first support portion 4 has a higher fastening force in the length direction L of the finger supporter 10 as compared with the base fabric portion 1 is satisfied.

Specifically, it is possible to increase the stretch resistance in the length direction L of the finger supporter 10 relative to the base fabric portion 1 that is a tuck-knitted fabric by using a knitted fabric obtained through tuck knitting and platting knitting in combination (hereinafter, referred to as tuck/platting-knitted fabric) for the first support portion 4.

Note that the tuck/platting-knitted fabric appropriately curbs stretchiness of the first support portion 4 in the length direction L of the finger supporter 10 by feeding yarn with other knitting yarn (for example, wooly nylon yarn) in addition to base knitting yarn for the tuck knitting, and other yarn is cut (cut both) at the boundary between the first support portion 4 and the base fabric portion 1.

Also, the first support portion 4 can support the thumb from the side of the first region 24a and prevent the thumb from dropping downward due to weakness in a case in which the palm is caused face sideways, by the first support portion 4 passing through the first region 24a of the thumb of the wearer from the vicinity of the second anchor portion 3 and being supported by the first anchor portion 2. In other words, it is possible to reduce a load on joints and muscles that support the thumb by lifting the thumb upward. On the other hand, it is possible to support the thumb from the side of the second region 24b and prevent the thumb from dropping downward due to weakness in a case in which the palm is caused to face sideways, by the first support portion 4 passing through the second region 24b of the thumb of the wearer from the vicinity of the second anchor portion 3 and being supported by the first anchor portion 2. In other words, it is possible to lift the thumb upward and to reduce a load on the joints and the muscles that support the thumb.

In particular, it is possible to more effectively lift the thumb upward and to reduce a load on the joints and the muscles that support the thumb in a case in which the palm is caused to face sideways, and also, the front side and the back side of the finger supporter 10 have a symmetrical relationship, which allows the supporter to be used for both left and right hands, by disposing the first support portion 4 to be supported by the first anchor portion 2 such that the first support portion 4 passes through the first region 24a and the second region 24b from the vicinity of the second anchor portion 3 in a Y shape, a V shape, a U shape, or other various forms in which the outer portion of the thumb is avoided, for example, in a form in which regions that pass on the back-of-hand side and the palm side are formed as two lines without being connected.

A corresponding thumb abutting region 13 of the first support portion 4 from the second anchor portion 3 to the metacarpophalangeal joint on the back-of-hand side of the thumb of the wearer is formed with a fabric with a weaker stretch resistance than the first support portion 4. Note that as the fabric with a weaker stretch resistance than the first support portion 4, the same fabric as that of the base fabric portion 1 may be used, or a fabric with a yet weaker stretch resistance than the base fabric portion 1 may be used, for example. It is possible to form the extended portion 12c more reliably adapted to the warp of the thumb by feeding the knitted fabric when the facing portion 12 is sewn using a sewing machine, by the thumb abutting region 13 being formed with the fabric with the weaker stretch resistance than the first support portion 4.

Note that even in a case in which the thumb abutting region 13 is formed with a fabric with the same stretch resistance as that of the first support portion 4, it is possible to form the extended portion 12c through the feeding of the knitted fabric when the facing portion 12 is sewn. However, in order to more reliably form the extended portion 12c with higher quality, it is desirable that the thumb abutting region 13 be formed with a fabric with a weaker stretch resistance than the first support portion 4.

Also, the fabric at the portion that abuts on the thumb on the back-of-hand side has high flexibility by the thumb abutting region 13 being formed with the fabric with a weaker stretch resistance than the first support portion 4, and it is possible to improve a feeling of wearing of the wearer.

Further, although the thumb abutting region 13 is formed into a Y shape when seen from the back-of-hand side of the thumb in FIGS. 1 to 4, the shape of the thumb abutting region 13 is not limited thereto as long as the first support portion 4 supports a portion from the second anchor portion 3 to the metacarpophalangeal joint of the thumb on the back-of-hand side with the structure.

The second support portion 5 is supported by the first anchor portion 2 in a region corresponding to the side surface on the little finger side of the wearer and supports the little finger side of the wearer. The second support portion 5 is formed such that a stretch resistance thereof in the length direction L of the finger supporter 10 is stronger than a stretch resistance of the base fabric portion 1 in the length direction L of the finger supporter 10. In other words, in a case in which the tensile force of the base fabric portion 1 in the length direction L of the finger supporter 10 is defined as $F_{L1}$, and the tensile force of the second support portion 5 in the length direction L of the finger supporter 10 is defined as $F_{L3}$, a magnitude relationship of $F_{L3}>F_{L1}$ that means that the second support portion 5 has a higher fastening force in the length direction L of the finger supporter 10 as compared with the base fabric portion 1 is satisfied. The second support portion 5 curbs excessive abduction, restricts a movable range, and more strongly supports the hand and the wrist in corporation with the first support portion 4, by supporting the side surface on the little finger side of the wearer between the first support portion 4 and the opening portion 12b.

Note that the stretch resistance of the second support portion 5 may be the same as the stretch resistance of the first support portion 4. It is thus possible to achieve the support from both the sides of the hand and the wrist, to achieve a balance between adduction and abduction, and to form the first support portion 4 and the second support portion 5 in the same process using the same knitted fabric.

As described above, since the finger supporter according to the embodiment includes the first anchor portion 2 that causes the tubular knitted fabric to be fastened to the forearm wrist portion of the wearer on one end side of the tubular knitted fabric formed through circular knitting, the second anchor portion 3 that is formed to sew the two points of the circling portion on the other end side of the tubular knitted fabric and forms the circling portion into the two opening portions (12a, 12b) with different sizes through the sewing, and the first support portion 4 that is supported between the second anchor portion 3 and the first anchor portion 2 and supports the thumb inserted into the smaller one of the opening portions from among the five fingers, it is possible to support the any finger of the wearer with the first support portion 4 and to reduce a load on muscles and joints that support the any finger.

Also, since the second anchor portion 3 is formed to be located between the metacarpophalangeal joint and the interphalangeal joint of the thumb on the palm side of the wearer, a tensile force of supporting the thumb from the palm side to the back-of-hand side is applied to the position between the metacarpophalangeal joint and the interphalangeal joint of the thumb with the first support portion 4, and it is possible to reduce a load on muscles and joints of the thumb on the palm side.

Further, since the first support portion 4 passes through the one side surface and/or the other side surface of the thumb of the wearer from the second anchor portion 3 and is then coupled to the first anchor portion 2 on the back-of-hand side, it is possible to stabilize the thumb of the wearer and to apply a sufficient tensile force on the back-of-hand side to the thumb.

Further, since the corresponding region from the second anchor portion 3 to the metacarpophalangeal joint of the thumb on the back-of-hand side of the wearer is formed with a fabric with a weaker stretch resistance than the first support portion 4, the supporter is not unnecessarily strongly fastened to the thumb of the wearer, and it is possible to improve a feeling of wearing.

Further, since the second support portion 5 that supports the region corresponding to the outer side of the little finger of the wearer is included, the little finger side is also stably supported in addition to the stabilization of the thumb, and it is possible to reduce a load on the entire hand.

Further, since the larger opening portion 12b into which the index to little fingers of the wearer are to be inserted out of the two opening portions (12a, 12b) with different sizes formed by the second anchor portion 3 is formed linearly or into an S shape in the oblique direction from the second anchor portion 3 toward the wrist side of the side surface on the little finger side of the wearer, it is possible to allow operations performed with finger tips on a keyboard, for example, to be smoothly performed. In particular, it is possible to bring the edge portion of the opening portion 12b into close contact with the surface of the thenar eminence such that the edge portion follows the surface of the thenar eminence, thereby improving a feeling of wearing of the wearer and enabling stable attachment, by forming the opening portion 12b into an S shape.

Note that although the second support portion 5 is included in the configuration in FIGS. 1 to 4 described above, a configuration in which the second support portion 5 is not included may also be employed.

Second Embodiment of Present Invention

A finger supporter according to the embodiment will be described with reference to FIGS. 1A-1E and 5 to 7. The finger supporter according to the embodiment is similar to the finger supporter according to the aforementioned first embodiment (FIGS. 1A-1E) but can be applied even to a case in which any one finger other than the thumb is inserted into the opening portion 12a, unlike the case illustrated in FIGS. 2 to 4. Note that the same description as that of the first embodiment will not be repeated in the embodiment.

Figure 5:
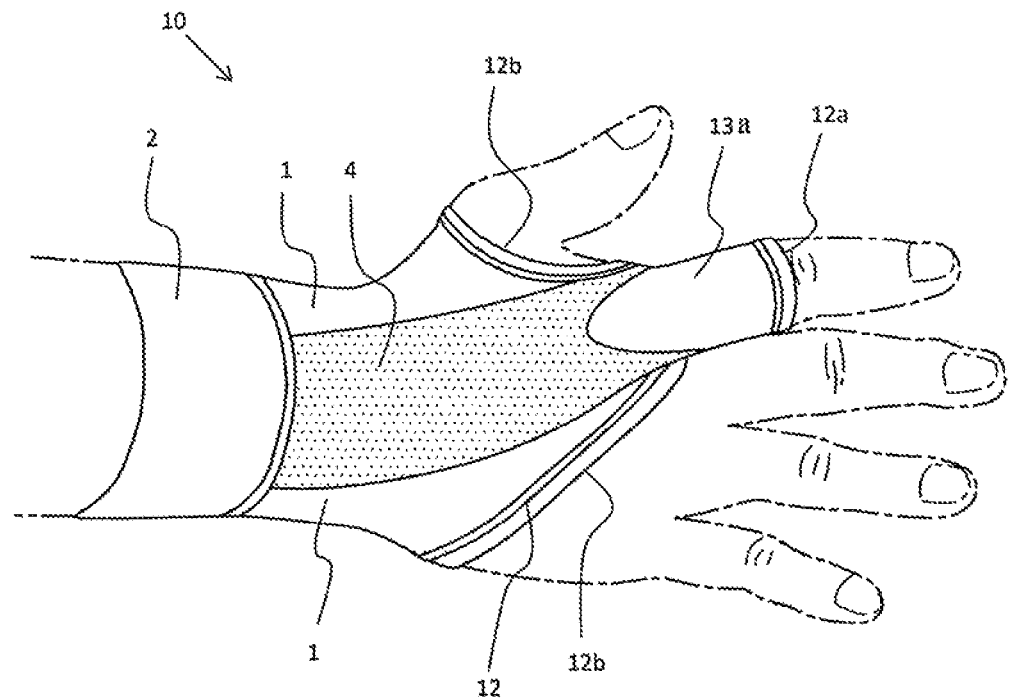
FIG. 5 is a first view illustrating a wearing state of a supporter according to a second embodiment.
Figure 6:
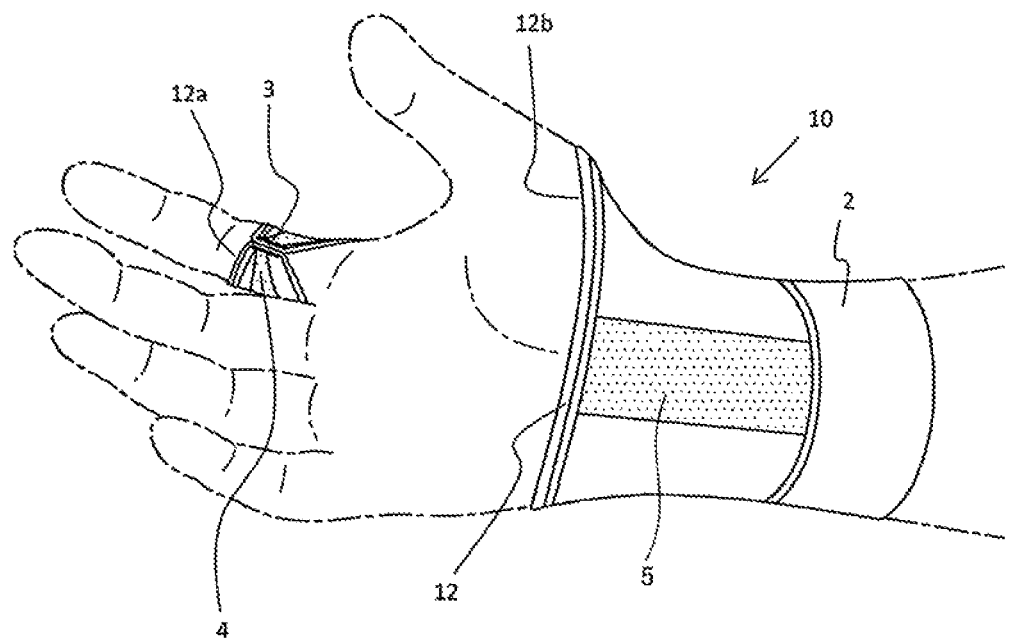
FIG. 6 is a second view illustrating a wearing state of the supporter according to the second embodiment.
Figure 7:
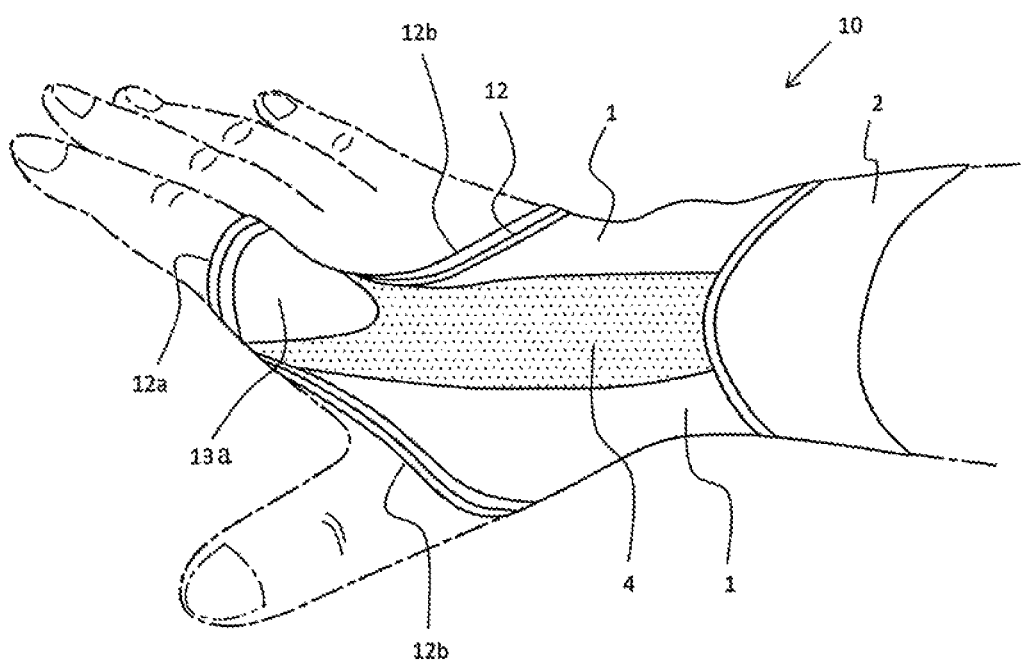
FIG. 7 is a third view illustrating a wearing state of the supporter according to the second embodiment.

FIGS. 5 to 7 are diagrams illustrating a wearing state in a case in which the finger supporter according to the embodiment is worn with the index finger inserted into the smaller opening portion 12a. Note that although FIGS. 5 to 7 illustrate the case in which the index finger is inserted into the opening portion 12a, any of other fingers, namely the thumb (as described in the first embodiment), the middle finger, the ring finger, or the little finger may be inserted.

As illustrated in FIGS. 5 to 7, the second anchor portion 3 is attached to be disposed between the metacarpophalangeal joint and the proximal interphalangeal joint of the wearer regardless of which of the fingers is to be inserted into the smaller opening portion 12a. It is thus possible to effectively lift each finger inserted into the opening portion 12a and the wrist on the back-of-hand side and to reduce a load on the hand.

Note that the finger to be inserted into the smaller opening portion 12a may be any one or two fingers from among the five fingers with the other fingers inserted into the larger opening portion 12b.

As described above, the finger supporter according to the embodiment allow any of the five fingers to be inserted into the opening portion 12a and can be used in various manners in accordance with a state of the wearer.

Note that elastic yarn used in the present invention is polyurethane-based or polyether ester-based elastic yarn. As the polyurethane-based elastic yarn, for example, dry-spined elastic yarn or melt-spined elastic yarn can be used, and a polymer and a spinning method are not particularly limited. Preferably, the elastic yarn has rapture elongation of about 400% to 1000%, has excellent stretchiness, and does not compromise the stretchiness at around a typical treatment temperature of 115° C. in a set process during a dying process. It is also possible to use elastic yarn to which functionality such as high setting properties, antibacterial properties, moisture absorbency, or water absorbency has been applied using a special polymer or adding powder. As for fineness of the elastic yarn, it is possible to use fiber with fineness of about 10 to 1000 dt, and it is preferable to use elastic fiber with fineness of about 20 to 700 dt that facilitates manufacturing of the knitted fabric. Moreover, it is also possible to use covering yarn obtained by winding non-elastic yarn around elastic yarn, twisted yarn, mixed yarn obtained by mixing non-elastic yarn and elastic yarn through air jetting, and the like.

As the non-elastic yarn used in the present invention, it is possible to use polyester-based fiber such as polyester or polytrimethylene terephthalate, polyamide-based fiber, synthetic fiber such as polypropylene, and further any types of fiber such as cellulose-based fiber including cupra, rayon, cotton, and bamboo fiber, and animal hair fiber such as wool. Also, it is possible to use any one of bright yarn, semi-dull yarn, full-dull yarn, and the like thereof, and as for the sectional shape of the fiber, it is possible to use fiber with any sectional shape such as a round shape, an oval shape, a W shape, a cocoon shape, or hollow yarn. In addition, the form of the fiber is not particularly limited, and it is possible to use raw thread, false-twisted crimped yarn, or the like. Further, it is also possible to use long fiber, spined yarn, or composite yarn obtained by mixing two or more types of fiber through twisting, covering, air mixing, or the like. Moreover, it is a matter of course that two or more types of fiber can be mixed on a knitting machine rather than just mixing the fiber, and it is only necessary to prepare yarn feeding ports corresponding to the two or more types of fiber in a weft knitting machine and to form the fabric. As for the thickness of the fiber, it is possible to use the fiber with a thickness of about 20 to 160 dt, and it is preferable to use the fiber with a thickness of about 20 to 150 dt in terms of breaking strength and a feeling of thickness of the knitted fabric. Note that it is only necessary to obtain the thickness of used fiber using a conversion expression when cotton or wool is used.

Further, the support portion 4 and the support portion 5 may be formed through plain knitting using nylon upper thread and rubber upper thread, for example. Filament twisted yarn (FTY) under thread may be knitted in the support portion 4 and the support portion 5 as needed. Also, the opening portions 12a and 12b may be formed through rib knitting.

Moreover, examples of the material for the finger supporter 10 according to the present invention includes: chemical fiber such as polyester, polypropylene, polyurethane, polyolefin, a polyolefin-based elastomer, polyamide, rayon, acryl, cupra, acetate, promix, aramid, and silicone; natural fiber such as cotton, wool, silk, hemp, rayon; natural rubber; polyvinyl chloride; and the like.

Further, the material configuring the finger supporter 10 according to the present invention is not particularly limited as long as the material is an elastic material with high stretchiness, and for example, a thermoplastic elastomer (such as a styrene-based elastomer, an olefin-based elastomer, a polyester-based elastomer, an urethane-based elastomer, a PVC-based elastomer, or a fluorine-based elastomer) and rubber (such as isoprene rubber, butadiene rubber, nitrile rubber, acrylic rubber, silicone rubber, or urethane rubber) may be used.

Moreover, the section of the yarn used in the finger supporter 10 according to the present invention may be a round section or a deformed section (for example, corners of a triangle are rounded, and sides thereof have curved shapes recessed inward).

Further, the first anchor portion 2 may include a spiral mesh.

REFERENCE SIGNS LIST

1 Base fabric portion
2 First anchor portion
3 Second anchor portion
4 First support portion
5 Second support portion
10 Finger supporter
10a Upper end
10b Lower end
12 Facing portion
12a, 12b Opening portion 12c Extended portion
13 Thumb abutting region
13a Index finger abutting region
23 Thenar eminence
24a First region
24b Second region

The invention claimed is:

1. A supporter comprising:
a first anchor portion that is formed on a first end side of a tubular fabric and configured to fasten the tubular fabric to a forearm wrist portion of a wearer;
a second anchor portion that forms a circling portion on a second end side of the tubular fabric opposite the first end side into a first opening portion and a second opening portion, the first and second opening portions having different sizes;
a first support portion positioned between the second anchor portion and the first anchor portion, the first support portion configured to support a finger or thumb of the wearer inserted into a smaller one of the first and second opening portions and having a first tensile force in a length direction of the tubular fabric between the first and second anchor portions;
a base portion positioned between the second opening portion and the first anchor portion, the base portion having a second tensile force in the length direction of the tubular fabric between the second opening portion and the first anchor portion; and
a second support portion spaced from the first support portion by the base portion,
wherein the first tensile force being greater than the second tensile force.

2. The supporter according to claim 1, wherein the second anchor portion is formed to couple two points of the circling portion on the second end side of the tubular fabric.

3. The supporter according to claim 1, wherein the second anchor portion is formed to be located between a metacarpophalangeal joint and a proximal interphalangeal joint or an interphalangeal joint of the finger of the wearer.

4. The supporter according to claim 1, wherein the first support portion passes through a side surface of the finger of the wearer from a vicinity of the second anchor portion and is supported by the first anchor portion.

5. The supporter according to claim 1, wherein a corresponding region from the second anchor portion to a metacarpophalangeal joint of the a finger on a back-of-hand side of the wearer is formed from a fabric that has a weaker stretch resistance than the first support portion.

6. The supporter according to claim 1, wherein the first support portion is configured to support the thumb, and second support portion supports a region corresponding to outside of a little finger of the wearer.

7. The supporter according to claim 1, wherein a larger opening portion of the first and second opening portions with different sizes formed by the second anchor portion is formed linearly or with a curve on a wrist side in an oblique direction from the second anchor portion toward the wrist side at a position of a peripheral edge of the larger opening portion which faces the second anchor portion.

8. The supporter according to claim 1, wherein a smaller opening portion of the first and second opening portions with different sizes formed by the second anchor portion is extended on an outer direction of the tubular fabric at least beyond a side surface of the first anchor portion of the tubular fabric.

9. The supporter according to claim 1, wherein the second anchor portion is formed by being sewn from outside with the two points on the inner side of the circling portion on the second end side of the tubular fabric.

10. The supporter according to claim 1, wherein the second end side of the tubular fabric has an S curved shape.

* * * * *